US 8,366,475 B2
Feb. 5, 2013

(12) United States Patent
Smith et al.

(54) DUAL DIRECTIONAL LATCH (75) Inventors: Kyle J Smith, Mission Viejo, CA (US); Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 13/239,153

(22) Filed: Sep. 21, 2011

(65) Prior Publication Data
US 2012/0034804 A1    Feb. 9, 2012

Related U.S. Application Data (63) Continuation-in-part of application No. 12/792,648, filed on Jun. 2, 2010, now Pat. No. 8,052,459.

(60) Provisional application No. 61/184,624, filed on Jun. 5, 2009.

(51) Int. Cl.
*H01R 13/62* (2006.01)
(52) U.S. Cl. ........................................ 439/372
(58) Field of Classification Search ............... 439/372, 439/345, 489, 953, 346–347, 668–669; 29/876, 29/874, 881, 825; 607/37
See application file for complete search history.

(56) References Cited

U.S. PATENT DOCUMENTS

| 5,076,270 | A * | 12/1991 | Stutz, Jr. ............... 607/37 |
| 7,070,455 | B2 * | 7/2006 | Balsells ............... 439/668 |
| 7,083,474 | B1 * | 8/2006 | Fleck et al. ............... 439/668 |
| 7,187,974 | B2 * | 3/2007 | Haeg et al. ............... 607/36 |
| 7,195,523 | B2 * | 3/2007 | Naviaux ............... 439/827 |
| 7,299,095 | B1 * | 11/2007 | Barlow et al. ............... 607/37 |
| 7,303,422 | B2 * | 12/2007 | Hoffer et al. ............... 439/359 |
| 7,429,199 | B2 * | 9/2008 | Burgess ............... 439/841 |
| 7,822,477 | B2 * | 10/2010 | Rey et al. ............... 607/37 |
| 2002/0122690 | A1 | 9/2002 | Poon et al. |
| 2003/0163171 | A1* | 8/2003 | Kast et al. ............... 607/36 |
| 2006/0224208 | A1* | 10/2006 | Naviaux ............... 607/37 |
| 2008/0254670 | A1 | 10/2008 | Balsells et al. |
| 2008/0255631 | A1 | 10/2008 | Sjostedt et al. |

FOREIGN PATENT DOCUMENTS

| GB | 2 194 298 A | 3/1988 |
| WO | WO 03/067713 A1 | 8/2003 |

OTHER PUBLICATIONS

Extended European Search Report from related European Patent Application No. 10005812.2 (6 pages), Sep. 27, 2010.

* cited by examiner

*Primary Examiner* — Jean F Duverne
(74) *Attorney, Agent, or Firm* — Klein, O'Neill & Singh, LLP (57) ABSTRACT

The present device, system, and method pertain to locking and/or latching mechanisms that utilize canted coil springs and specific groove geometries in connecting parts to achieve locking and/or latching. In specific locking and/or latching embodiments, built in release features are provided to enable unlatching even after being locked, such as by moving in the opposite direction as when moving the connector to lock. Unlatching can implemented by rotating the spring to permit moving in the opposite direction.

24 Claims, 6 Drawing Sheets

DUAL DIRECTIONAL LATCH

CROSS-REFERENCE TO RELATED APPLICATIONS

This is a continuation-in-part application of application Ser. No. 12/792,648, filed Jun. 2, 2010 now U.S. Pat. No. 8,052,459, which is a regular application of provisional application Ser. No. 61/184,624, filed Jun. 5, 2009, the contents of each of which are expressly incorporated herein by reference.

FIELD OF ART

The present device, system, and method pertain to locking and/or latching mechanisms that utilize canted coil springs and specific groove geometries in connecting parts to achieve locking and/or latching. In specific locking and/or latching embodiments, built in release features are provided to enable unlatching even after being locked, such as by moving in the opposite direction as when moving the connector to a lock position, as further discussed below.

BACKGROUND

Conventional connection mechanisms utilize a canted coil spring and specific groove geometries between a first connector component and a second connector component, such as a housing and a pin, to achieve locking or latching, see, for example, U.S. Pat. Nos. 4,678,210 and 5,082,390. In the case of a locking device, the device becomes permanently locked, which means the device cannot reverse direction without permanently damaging the canted coil spring. In the case of a latching device, the device can be unlatched, i.e., reverse direction, without damaging the spring. This is permitted by incorporating a groove geometry that allows the minor axis to compress.

Locking is achieved between two mating parts (e.g., cylindrical part or shaft and housing) where a tapered bottom groove exists in the housing and holds an axial spring and where the tapered bottom groove aligns with a corresponding groove on the cylindrical part which accepts the spring. The tapered bottom groove is configured in such a way that the spring compresses along the minor axis upon insertion to permit installation but not upon removal when moving in the reverse direction. Because the spring does not compress along the minor axis upon removal, it does not unlatch and remain locked. The spring is forced to compress along the major axis when attempting to remove the cylindrical part, which does not materially or significantly compress, to ensure locking. As such, removal of a "locked" device causes permanent damage to the spring if forced to disassemble. Again, this is due to the characteristic of a canted coil spring only being allowed a minimal compression along the major axis.

SUMMARY

The present device, system, and method make it possible for a locking connection to be disconnected when moving in the reverse or opposite direction, which previously was not possible without damaging the spring, as discussed above. In one example, the device, system, and method include incorporating or providing a sufficiently deep secondary groove in addition to a primary groove to allow the canted coil spring to rotate back to its relaxed vertical position. Unlike when in the primary groove, the spring is not held when in the secondary groove against rotation and has room to rotate in the opposite direction that it experienced during insertion. The leading edge of the secondary groove makes contact with the canted coil spring and rotates it in the tapered bottom groove of the secondary groove along the minor axis towards the shallow end, thus allowing for removal of the canted coil spring from the secondary groove and back into the first groove, but being rotated for removal or unlocking. Here the canted coil spring is orientated so that the cylindrical part can be completely unlatched.

Thus, once the cylindrical part is inserted into the housing and engages the primary groove, the canted coil spring experiences a removal lock, i.e. it cannot be removed by moving the cylindrical part in the reverse direction without damaging the spring, also referred to as a single step lock. To unlock the assembly, essentially by converting a locking device into a latching device that permits unlocking or unlatching, the spring is rotated to permit reversal of the cylindrical part. In an example, the cylindrical part is further inserted into the housing in the same direction as the original direction for locking to permit spring rotation. During the further insertion step, the spring engages a secondary groove, which is larger than the primary groove. By larger, it is understood to mean wider, deeper, or both wider and deeper than the primary groove. Because the secondary groove is larger, the spring is not so constrained and permitted to rotate. Preferably, the secondary groove does not restrain the spring. From this point with the secondary groove, the device can be unlatched by moving the cylindrical part in the removal direction. Thus, the device is capable of dual directional latching.

The combination primary and secondary grooves may optionally be incorporated in the housing or the cylindrical part. In other words, the same component, i.e. housing or cylindrical part, has both the primary groove and the secondary groove and the spring moves between the two grooves to unlatch after locking.

In addition to allowing dual directional latching, the larger secondary groove following the primary groove can provide a lower removal force as compared to removal from the primary groove in latching applications.

Thus, once the cylindrical part is inserted into the housing and engages the primary groove, the canted coil spring experiences a removal lock. To unlatch, the cylindrical part is first inserted further into the housing. In one example, when the pin is further inserted, a secondary groove located on the pin moves into the housing so that the spring engages the secondary groove. In a specific example, the second groove is larger than the first groove. Once in the larger second groove, the spring is able to rotate and be unlatched by moving the cylindrical part in the removal direction, opposite the insertion direction. By larger, the groove can have a larger groove depth, a larger volumetric space, or both.

A still further feature of the present device, system, and method is understood to include a connector comprising a pin located inside a bore of a housing by inserting the pin into the bore of the housing in a first direction; preventing the pin from moving in a second direction, opposite the first direction, by positioning a spring located inside a groove defined by a housing groove and a primary groove on the pin; and wherein the pin is permitted to move in the second direction by first further moving the pin in the first direction before it could be moved in the second direction. In a particular embodiment, the canted coil spring located inside the first groove of the pin is rotated and moves to a second groove on the pin before the pin is able to move in the second direction.

An exemplary connector provided herein is understood to comprise a housing comprising a bore comprising a housing groove comprising a housing groove depth. A pin comprising a pin groove comprising a pin depth is disposed in the bore of the housing. A canted coil spring is retained within a connector groove defined by the housing groove and the pin groove in a first spring position. The connector further comprises a second groove for accommodating the canted coil spring located adjacent at least one of the housing groove and the pin groove.

An exemplary method provided herein is understood to comprise a method for mating a pin in a bore of a housing. In certain examples, the method comprising the steps of moving the pin, which comprises a first pin groove and a second pin groove, in a first direction and locking the pin to the housing by preventing withdrawal of the pin in a second direction, which is opposite the first direction. The housing comprising a housing groove. The method further comprising positioning a canted coil spring concurrently in the first pin groove and the housing groove at a first turn angle so that a major axis of the canted coil spring is compressed to move the pin in the second direction. The method further comprising moving the pin in the first direction into the bore of the housing from a first position relative to the housing to a second position relative to the housing to locate the canted coil spring in the second pin groove. The method still further comprising moving the pin in the second direction after positioning the canted coil spring in the second pin groove so that the canted coil spring is re-positioned in the first pin groove.

The device is further understood to include a connector comprising a housing comprising a bore and a housing groove and a pin comprising a first pin groove having a first groove depth and a second pin groove comprising a second groove depth, which is larger than the first groove depth. The connector wherein a canted coil spring is engageable with the first pin groove to lock the pin to the housing, and wherein the canted coil spring is engageable with the second pin groove to permit rotation of the canted coil spring to allow separation of the pin from the housing.

Thus, aspects of the present device, system, and assembly are understood to include a structure having a combination primary groove and secondary groove, located next to the primary groove, and wherein the primary groove is shaped with a first dimension for locking and preventing rotation of a spring major axis and the secondary groove is shaped with a second larger dimension to permit rotation of the spring major axis. In other examples, one or more grooves may be located between or adjacent the primary groove and the secondary groove. When other grooves are incorporated in addition to the primary and secondary grooves, the connector is understood to include multiple grooves wherein a larger groove following a relatively smaller groove is provided to permit rotation of the spring to enable reversing direction of movement of the pin or the housing for unlatching following locking.

The canted coil spring discussed herein is preferably an axially canted coil spring. In other embodiments, the spring is a radially canted coil spring. When a radially canted coil spring is incorporated, the grooves are understood to be correspondingly modified to require compressing the coil along an appropriate axis to lock and unlatch.

SUMMARY OF THE DRAWINGS

The various embodiments of the present connectors, systems, and associated methods now will be discussed in detail with an emphasis on highlighting the advantageous features. These embodiments depict the novel and non-obvious connector shown in the accompanying drawings, which are for illustrative purposes only. These drawings include the following FIG.s, in which like numerals indicate like parts.

DETAILED DESCRIPTION

The following detailed description describes the present embodiments with reference to the drawings. In the drawings, reference numbers label elements of the present embodiments. These reference numbers are reproduced below in connection with the discussion of the corresponding drawing features.

The embodiments of the present connectors, systems, and associated methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unit or a unitary piece and whereas a unitary piece means a singularly formed single piece, such as a singularly formed mold or cast. Still further, the terms "first" and "second" used herein are understood as identifiers only to distinguish between similar but different components. Thus, unless the context indicates otherwise, "first" and "second" are not limiting terms.

Figure 1:
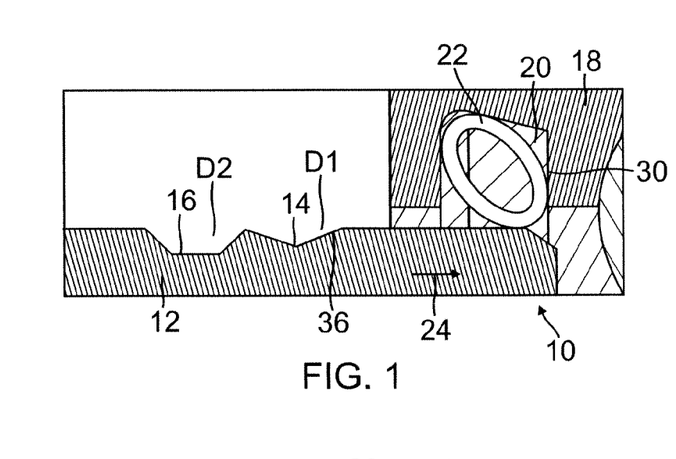
FIG. 1 shows a schematic cross-sectional side view of a dual direction connector, which shows a pin moving into a bore of a housing.

FIG. 1 shows a partial cross-sectional side view of a connector provided in accordance with aspects of the present device, system and method, which is generally designated 10. The connector is symmetrical about a center line of the pin 12. In one example, the pin 12, also referred to as a shaft or a cylindrical insert, comprises a primary groove 14 and a secondary groove 16. The pin preferably incorporates a tapered nose section 11 to facilitate insertion of the pin into a bore of the connector housing 18. In the example shown, the primary groove 14 comprises a bottom wall having a depth measured from the pin outer surface of D1 and the secondary groove 16 comprises a bottom wall having a depth measured from the pin outer surface of D2. In a particular example, the secondary groove 16 is larger than the primary groove 14 and D2 is greater than D1. The bottom wall of the primary groove may be flat or tapered, as further discussed below. Similarly, the bottom wall of the secondary groove may be flat or tapered.

The pin 12 is shown being inserted into the stationary housing 18, which has a housing groove 20 and a canted coil spring 22 being disposed therein. The spring 22 is angled and compressed upon insertion caused by contact with the entry 11 of the cylindrical insert 12. The spring 22 has a major axis, defined by the larger axis of the coil, and a minor axis, defined by the smaller axis of the coil, which is perpendicular to the major axis. In one example, the pin has a round cross-section. In other embodiments, the pin has a square cross-section, an oval cross-section, or a polygon cross-section.

The housing groove 20 comprises a first sidewall 30, a second sidewall 32, and a bottom wall 34, which is preferably tapered or angled relative to either of the two sidewalls. In one example, the bottom wall 34 tapers downwardly in the direction of insertion, also sometimes referred to as the first direction.

Figure 2:
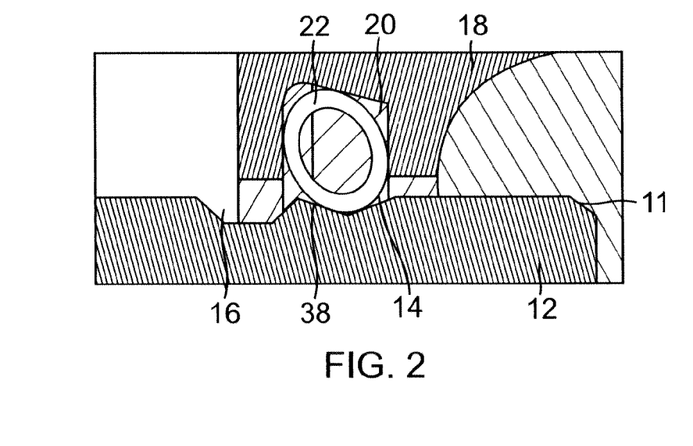
FIG. 2 shows a schematic cross-sectional side view of the dual direction connector of FIG. 1 in which the pin is secured in the housing by positioning a canted coil spring in a groove defined by the housing and the pin.

FIG. 2 shows the spring 22 located in the initial or primary groove 14 in the cylindrical part 12 and the housing groove 20. In this position, as in traditional locking applications, removal of the cylindrical part 12 would require the spring 22 to compress along the major axis, which if carried out would require a relatively large force and cause the spring to be permanently damaged. In one example, the spring 22 is rotated so that its major axis, defined by the longer dimension of the spring, faces the tapered wall surface 36 of the primary groove 14 and between sidewall 32 and tapered bottom surface 34 of the housing groove 20. In this configuration, the normally non-compressible major axis needs to collapse in order to permit removal of the pin 12 in a second direction, opposite the first direction 24 (FIG. 1). However, such compression is not possible without damaging the spring.

Figure 3:
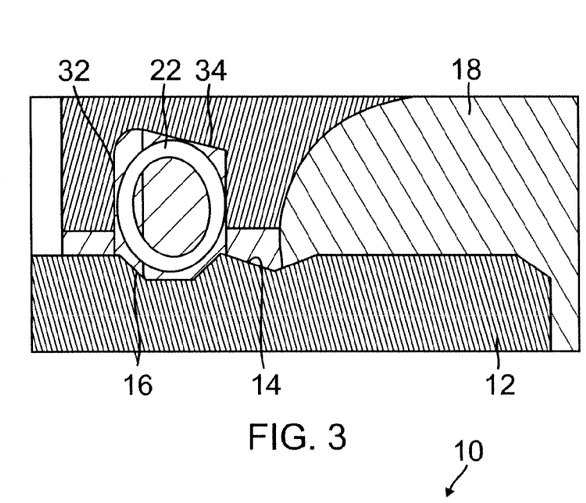
FIG. 3 shows a schematic cross-sectional side view of the dual direction connector of FIG. 2 wherein the spring is moved to a second groove defined by the housing and the pin and rotated.
Figure 4:
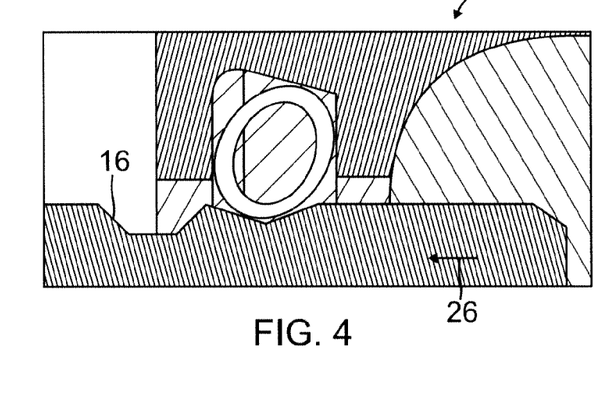
FIG. 4 shows a schematic cross-sectional side view of the dual direction connector of FIG. 3 wherein the pin is moved in a second direction and the spring moves from the second pin groove back into the first pin groove in the direction of the arrow.

FIG. 3 shows the spring 22 being moved beyond the initial groove 14 by moving the cylindrical part 12 further into the housing 18 in the direction of the arrow 24 of FIG. 1, i.e., further in the first direction. As the spring 22 is already turned in the first direction in its normal operating turn angle, further insertion of the pin in the first direction 24 is permitted. In one example, the second tapered wall surface 38 of the primary groove 14 is angled to exert a force in the direction of the minor axis of the spring, which is orthogonal to the major axis, to permit further movement in the first direction. In one example, the primary groove 14 comprises a V-groove. The spring 22 now latches into the secondary groove 16 and the housing groove 20. The secondary groove 16, being deeper and larger than the initial groove 14, does not maintain contact with the spring 22 and the spring is allowed to relax and straighten out. In other embodiments, the secondary groove 16 does contact the spring but also provides sufficient depth for the spring to relax and straighten out. From this point, the cylindrical part 12 can be removed since the spring 22 has room to rotate in the opposite direction, similar to performing an insertion in the opposite direction, and properly compress along the minor axis back into the first groove 14 as the pin is withdrawn. FIG. 4 shows the spring rotated in a correct orientation that allows the assembly to unlatch when moving in the second direction 26, which is opposite the first direction. Further movement of the pin in the second direction 26 from the perspective of FIG. 4 will permit complete removal from the housing 18.

Thus, an aspect of the present device, system and method is understood to include a connector comprising a cylindrical insert comprising a first groove having a first groove depth and a second groove comprising a second groove depth, which is larger than the first groove depth, and wherein a spring is engageable with the first groove to lock the cylindrical insert with a housing comprising a housing groove, and wherein the spring is engageable with the second groove to permit rotation of the spring to allow separation of the cylindrical insert from the housing.

A further aspect of the present device, system, and method is understood to include a method for inserting a cylindrical insert into a bore of a housing in a first direction and locking the cylindrical insert to the housing by preventing withdrawal of the cylindrical insert in a second direction, opposite the first direction. Said method comprising inserting said cylindrical insert, which comprises a first groove and a second groove, into the housing in a first direction to position a spring in the first groove and preventing removal of the cylindrical insert in the second direction by turning the spring to require compressing the spring along a major axis. The method further comprising moving the cylindrical insert in the first direction into the housing from a first position relative to the housing to a second position relative to the housing to position the spring in the second groove. The method further comprising moving the cylindrical insert in a second direction to re-position the spring in the first groove and removing the cylindrical insert from said housing such that the cylindrical insert is no longer located in a bore of the housing.

A further aspect of the present device, system, and method is a cylindrical insert comprising an insertion end, a first groove located proximate the insertion end, and a second groove located proximate the first groove and further away from the insertion end than the first groove, and wherein the first groove comprises a first depth and the second groove comprises a second depth, which is deeper than the first depth. Depth is a relative term and is understood to mean with reference to the outer surface of the pin along a nominal outer diameter of the pin.

A still further aspect of present device, system, and assembly is a connector comprising a pin comprising a first groove and a second groove and a housing comprising a housing groove. The pin is configured to be inserted into a bore of the housing when moving in a first direction. The device, system, and assembly wherein a spring is configured to be positioned between the first groove and the housing groove in a first position, between the second groove and the housing groove in a second position, and between the first groove and the housing groove in a third position. The device, system, and method wherein when the spring is in the first position, the pin is locked to the housing and removal of the pin from the housing by moving the pin in a direction opposition to the first direction is prevented without compressing the spring along its major axis. The device, system, and method wherein when the spring is in the second position, the spring is rotated from a turned angle from when the spring is in the first position. The device, system, and method wherein when the spring is in the second position, the spring does not contact the housing groove. In one example, the spring is in a second turned angle when in the second position. The device, system, and method wherein when the spring is in the third position, the spring is rotated to a third turned angle.

In yet another aspect of the present device, system, and method, a pin is provided comprising a single groove comprising a tapered bottom surface and two sidewall surfaces that are parallel to one another. The device, system, and method further comprising a housing comprising bore comprising a first housing groove located near an inlet opening and a second housing groove located adjacent the first housing groove and further away from the inlet opening than the first housing groove. The device, system, and method, wherein the second housing groove is larger than the first housing groove. In one example, the first housing groove has a depth D1 and the second housing groove has a depth D2, both measured relative to an inside nominal diameter of the bore; and wherein D2 is deeper or larger than D1. In an embodiment, the first housing groove incorporates the groove geometry of the primary pin groove 14 and the second housing groove incorporates the groove geometry of the secondary pin groove 16.

In one example, the housing 18 is made from a metallic material. In another example, the metallic material, which may be a highly conductive metal such as aluminum, aluminum alloys, copper, copper alloys, noble metals, noble metal alloys, or silver, is coated with an outer conductive material. For example, the inner metal layer may be coated or plated with an outer stainless steel layer, which has high tensile strength than the inner metal layer. In another embodiment, the inner conductive layer is made from a high tensile strength material, such as stainless steel, and the out coated or plated material is made from a highly conductive material, such as aluminum, aluminum alloys, copper, copper alloys, noble metals, noble metal alloys, or silver. In another embodiment, the canted coil spring 22 and optionally the pin 12 are made from multi-metallic materials having material combinations discussed herein. Exemplary bi-metallic and multi-metallic connectors are disclosed in co-pending application Ser. No. 12/767,421, filed Apr. 26, 2010, and US Publication No. 2008/0254670, the contents of which are expressly incorporated herein by reference. In another application, for non-electrical transmission, the housing 18 is made from a thermoplastic or an engineered plastic material.

Exemplary applications for the connectors disclosed herein include aerospace industry, for automotive industry, for oil and gas industry, for consumer electronics industry, for medical device industry, and for green technology, such as for wind mill and solar panel applications. For these industries, the disclosed system, device, and method may be used to connect wires or cables together.

Figure 5:
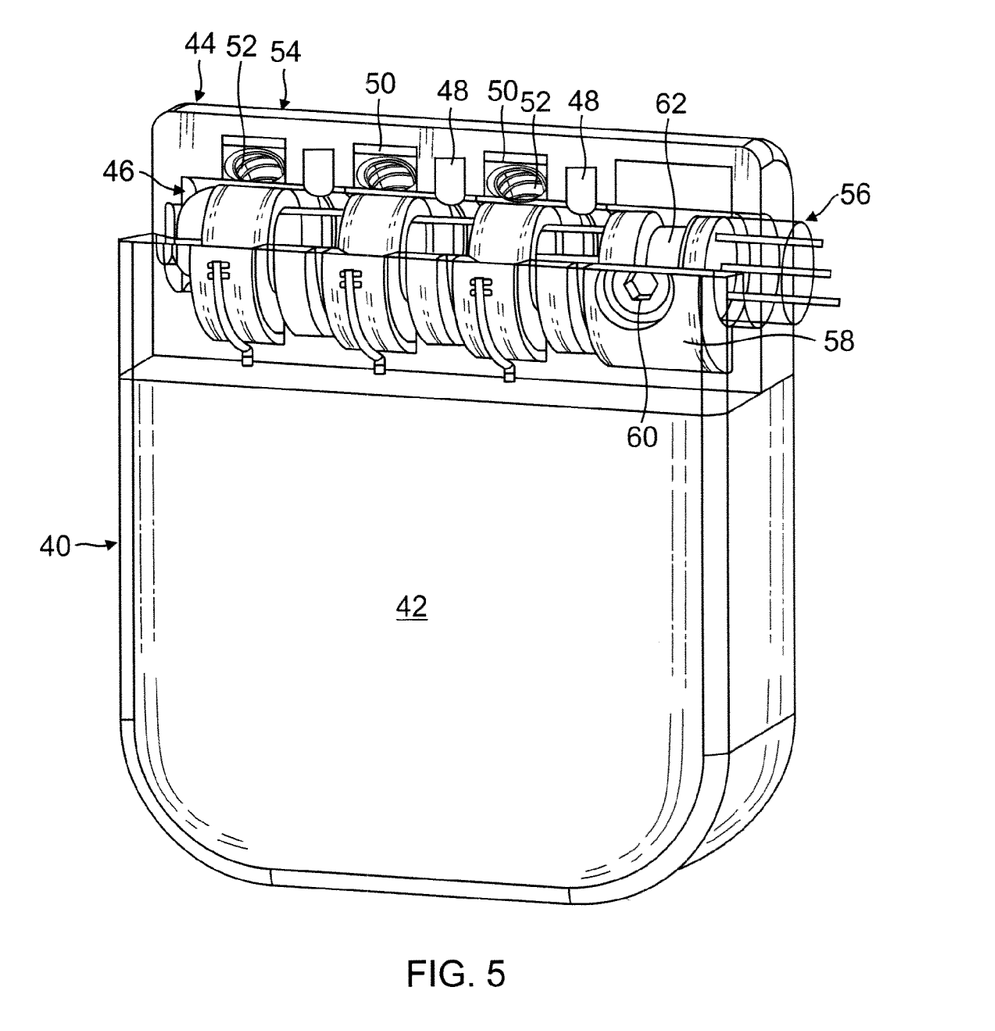
FIG. 5 is a partial cut-away perspective view of an implantable medical device comprising a sealed housing and an in-line connector located in a header.

Turn now to FIG. 5, a schematic partial cut-away perspective view of an implantable medical device (IMD) is shown, which can include implantable cardio defibrillators, pacemakers, and programmable neurostimulator pulse generators. The IMD comprises a sealed housing 42, which is known in the industry as a can or canned housing, and a header 44 comprising an in-line connector 46. The in-line connector 46 comprises a plurality of alternating seal elements 48 and conductive elements 50, of which only three alternating sets are shown. Canted coil springs 52 are also incorporated, one in contact with each of the conductive elements 50. The header housing 54, the springs 52, the conductive elements 50, and the seal elements 48 have a common bore for receiving a lead cable 56. The lead cable 56 has terminal ends (not shown) that are positioned near an area to be treated, such as near the heart for a cardiac heart pacemaker application. The cable 56 is configured to carry signals away from the canned housing 42 or vice versa for a therapeutic monitoring application. Additional information regarding IMDs and in-line connectors are disclosed in US Publication numbers 2008/0246231 and 2008/0255631, which are expressly incorporated herein by reference. Other IMDs and in-line connectors are also disclosed in co-pending application Ser. Nos. 12/717,732, filed Mar. 4, 2010, and 12/618,493, filed Nov. 13, 2009, the contents of each of which are expressly incorporated herein by reference.

To secure the lead cable 56 within the bore of the header, a retention block 58 is used, which comprises a set screw 60 for fastening against a corresponding surface 62 on the lead cable, which is analogous to a pin groove. The retention block 58 may be located at the inlet of the header 44, as shown, or at the far end of the header. In accordance with an aspect of the present device, system, and method, the connector 10 of FIGS. 1-4 is used in place of a combination retention block 58 and pin groove 62 on a lead cable 56 of a header of an IMD. For example, the housing 18 of FIGS. 1-4 may be used in place of the retention block 58 of FIG. 5 and instead of a single pin groove 62, a primary groove and a secondary groove are used for the lead cable, similar to that shown on the pin 12 of FIGS. 1-4. Furthermore, the connector may be placed near the inlet as shown in FIG. 5 or at the far end of the header. Still furthermore, the modified retention mechanism may incorporate a single pin groove on the lead cable and two housing grooves for the retention block, as discussed above in the alternative configuration.

Figure 6:
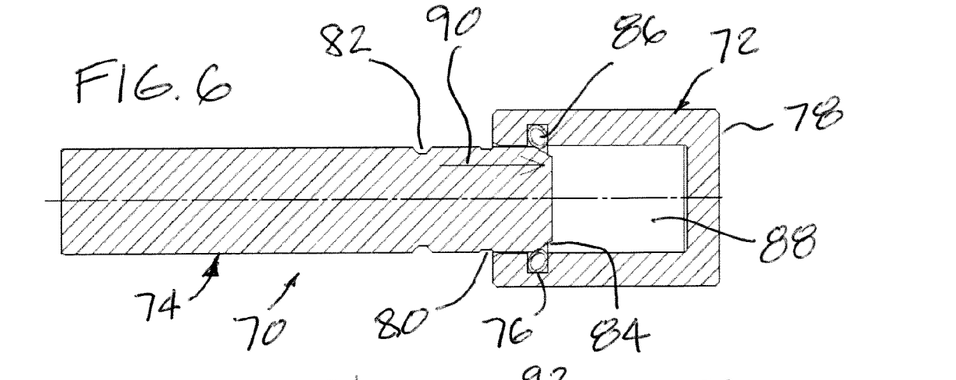
FIG. 6 is a schematic cross-sectional side view of an alternative connector at the start of its insertion or connection step.

FIG. 6 shows a connector 70 provided in accordance with aspects of the present device, system, and method, which includes a housing 72 and a cylindrical part 74, such as a pin, rod, or shaft. The housing 72 has a housing groove 76 and an enclosed end 78, which may optionally be opened. The groove 76 has two side walls and a bottom wall located therebetween. The groove 76 is preferably non-tapered or square with two generally parallel sidewalls and a bottom wall that is roughly right angle to the sidewalls. Said differently, the bottom wall has a bottom surface or wall that is generally parallel to a longitudinal axis of the housing. If the groove is located on the cylindrical part, the flat bottom wall is generally parallel to a longitudinal axis of the cylindrical part. Optionally, one or both sidewalls may be angled, i.e., not right angle, relative to the bottom wall.

The cylindrical part 74 has a primary groove 80, a secondary groove 82, and a leading edge 84, which is preferably tapered. The primary and secondary grooves are shown with the cylindrical part. In another example, the cylindrical part 74 has a single groove, with a flat bottom wall, and the housing incorporates a primary groove and a secondary groove. The primary groove, the secondary groove, or both are shaped like a truncated "V" with the apex of the "V" being a flat bottom wall. In another embodiment, the secondary groove has a single tapered wall but the groove is sufficiently deep to permit rotation of the spring, as further discussed below. The single tapered wall is preferably the wall closer to the primary groove. Although the bottom wall of the secondary groove is shown with a flat bottom, it may be tapered.

FIG. 6 shows a spring 86 being rotated and temporarily fixed at a certain angle relative to the housing groove 76. The leading edge 84 of the cylindrical part compresses the spring 86 upon insertion of the cylindrical part 74 in the direction of the arrow 90 into the bore 88 of the housing 72. The housing 72 and the cylindrical part 74 may be referred to as a first connector component and a second connector component, wherein the terms "first" and "second" merely identify the components as being two separate connector components and therefore can be used in the reverse sense. For example, the first connector component can be the cylindrical part and the second connector component can be the housing.

Figure 7:
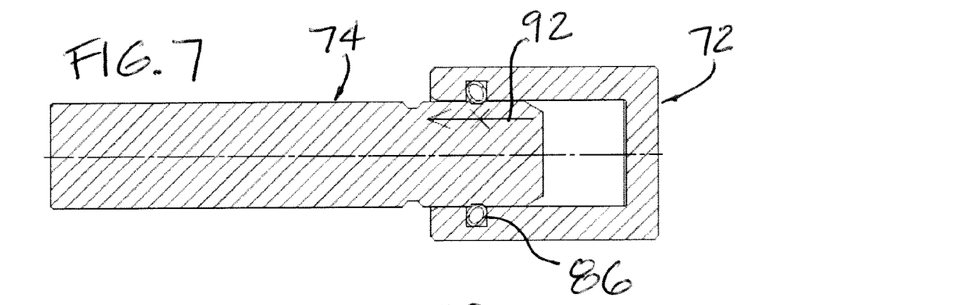
FIG. 7 is a schematic cross-sectional side view of the connector of FIG. 6 showing a first connector element further inserted into a second connector element and capturing a spring in between two grooves.

FIG. 7 shows the spring 86 in the primary or initial groove 80 in the cylindrical part 74. In this position, the minor axis of the spring could not be compressed by moving the cylindrical part in the direction of the removal arrow 92, which is opposite or reverse of the insertion arrow 90. As such, any attempt to move the cylindrical part 74 in the direction of the removal arrow 92, as in traditional locking applications, would require compressing the spring along the major axis to provide clearance for moving the cylindrical part relative to the housing. However, this would require a much larger force than compressing the minor axis of the spring as the major axis does not materially compress. Accordingly, any attempt to remove the cylindrical part would cause permanent damage to the spring 86.

Figure 8:
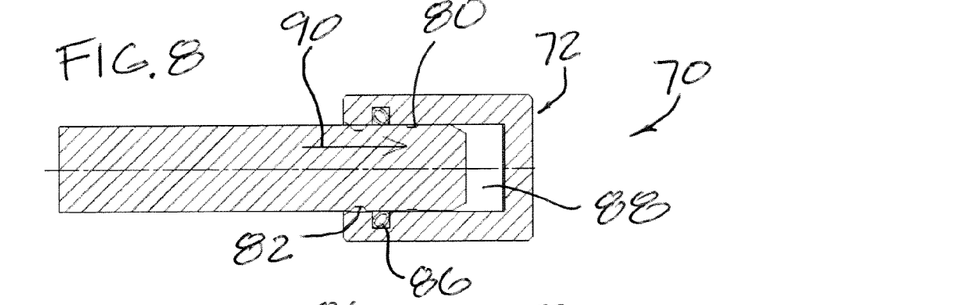
FIG. 8 is a schematic cross-sectional side view of the connector of FIG. 6 showing the first connector element further inserted into the second connector element, beyond the position shown in FIG. 7, so that the spring is now located in between the first groove and the second groove of the first connector element but still retained in the groove of the second connector element.

FIG. 8 shows the cylindrical part 74 further moved into the bore 88 of the housing 72 in the direction of the insertion arrow 90. This is possible due to the position or angle of the major axis relative to the direction of movement of the cylindrical part 74. When moving in the direction of the insertion arrow 90, the primary groove 80 lifts the spring 86, i.e., compresses the spring along the minor axis, to permit the spring to pass over the primary groove 80. In contrast, as discussed with reference to FIG. 7, moving the cylindrical part 74 when engaged to the primary groove along the removal arrow 92 is not possible because it would require lifting or compressing the major axis. As shown in FIG. 8, the spring 86 is positioned against a flat surface on the cylindrical part, between the primary groove 80 and the secondary groove 82. In this position, the spring is said to be holding the housing and the cylindrical part by its spring force, which is also dependent on surface friction. Thus, aspects of the present device, system, and method, include a connector that has spring located in a first groove for locking, the spring being moved to a location adjacent the first groove for holding, and the same spring being movable to a second groove for latching, and wherein a housing groove has a flat bottom wall located between two side walls. In another example, a connector is provided that has spring located in a first groove for locking, the spring being moved to a location adjacent the first groove for holding, and the same spring being movable to a second groove for latching, and wherein a cylindrical part comprises a groove with a flat bottom wall located between two side walls.

Figure 9:
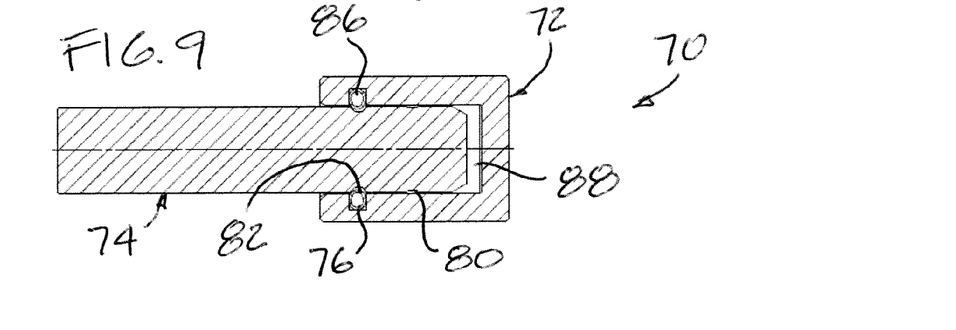
FIG. 9 is a schematic cross-sectional side view of the connector of FIG. 6 showing the first connector element still further inserted into the second connector element, beyond the position shown in FIG. 8, so that the spring is now captured between the second groove of the first connector element and the groove of the second connector element.

FIG. 9 shows the spring 86 latched between the housing groove 76 and the secondary groove 82. In the example shown, the secondary groove 82 is sufficiently deep and does not maintain contact with the spring 86. Thus, the spring 86 is allowed to relax and straighten out. From this point of the moving cycle, the cylindrical part 74 can be removed since the spring has room to rotate in the opposite direction of insertion. Once rotated in the opposite direction, such as when moving the cylindrical part in the direction of the removal arrow 92 from the position shown in FIG. 4, the spring can properly compress along the minor axis in the housing groove 76.

Figure 10:
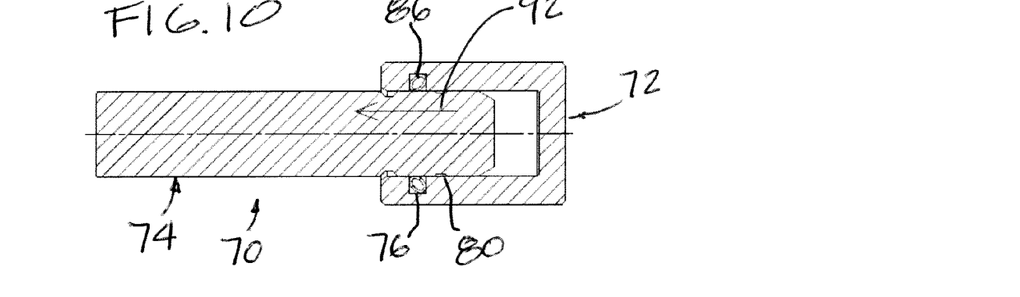
FIG. 10 is a schematic cross-sectional side view of the connector of FIG. 6 showing the first connector element reversing direction to separate from the second connector element.

FIG. 10 shows the spring 86 rotated in a correct orientation that allows complete removal of the cylindrical part. Thus, even though the spring 86 will eventually move back into the primary groove 80 upon moving the cylindrical part in the direction of the removal arrow 92, the rotated major axis permits the spring to compress against the primary groove 80 and allow the cylindrical part to be completely removed. Said differently, when the canted coil spring is located in the primary groove for a second time, after being separated from the primary groove, it can compress along a minor access to permit unlatching. Thus, aspects of the present device, system, and method, include a connector that has spring located in a first groove for locking, the spring being movable to a location adjacent the first groove for holding, and the same spring being movable to a second groove for latching, and wherein a housing groove has a flat bottom wall located between two side walls. The connector further comprises provisions or steps for returning the spring to the first groove but permitting the spring to compress to unlock the cylindrical part and the housing from one another.

In another example, a connector is provided that has spring located in a first groove for locking, the spring being movable to a location adjacent the first groove for holding, and the same spring being movable to a second groove for latching, and wherein a cylindrical part comprises a groove with a flat bottom wall located between two side walls.

Figure 11:
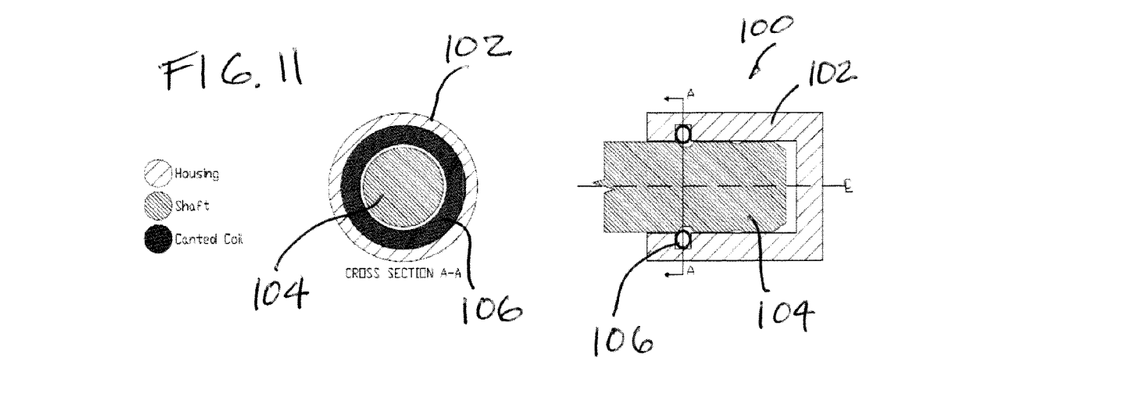
FIG. 11 is a schematic cross-sectional side view and end view of an alternative connector.

FIG. 11 shows a side and cross sectional view of a connector 100 having a pin 104, a housing 102, and a spring 106. The pin and the housing have a generally circular cross section. The connector 100 may lock and unlatch or unlock in the some manner as discussed above for the connector 70 of FIGS. 6-10.

Figure 11A:
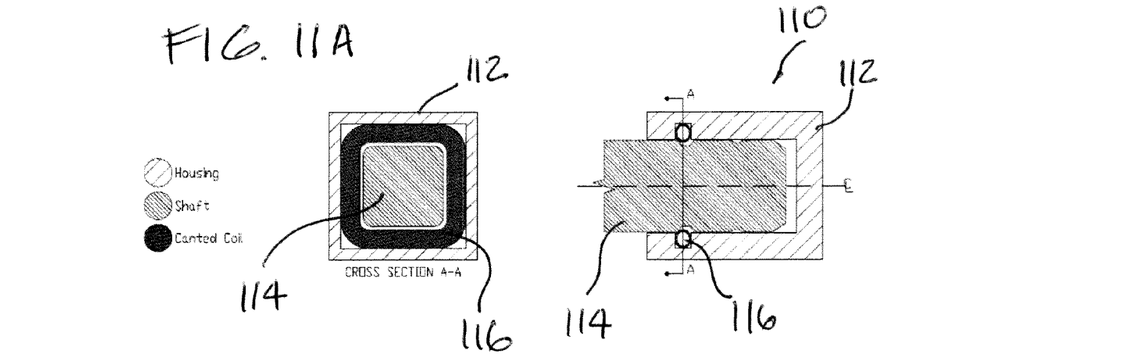
FIG. 11A is a schematic cross-sectional side view and end view of yet another alternative connector.

FIG. 11A shows a side and cross sectional view of a connector 110 having a pin 114, a housing 112, and a spring 116. The pin and the housing have a generally square cross section. The connector 110 may lock and unlatch or unlock in the same manner as discussed above for the connector 70 of FIGS. 6-10.

Figure 11B:
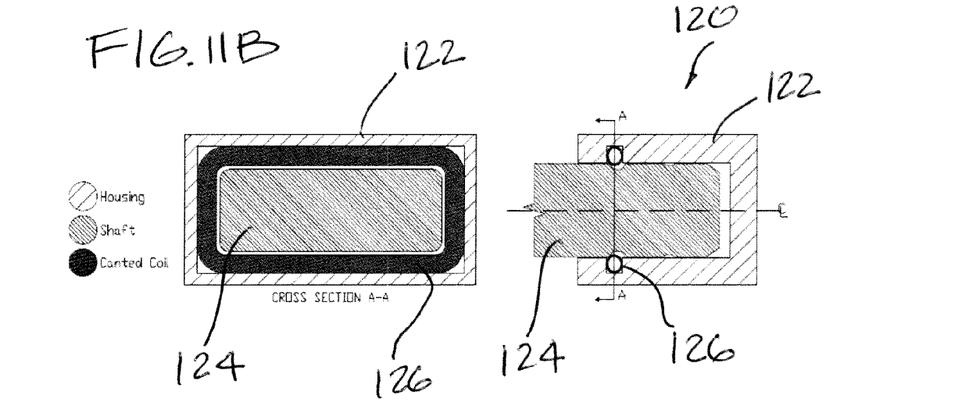
FIG. 11B is a schematic cross-sectional side view and end view of yet another alternative connector.

FIG. 11B shows a side and cross sectional view of a connector 120 having a pin 124, a housing 122, and a spring 126. The pin and the housing have a generally rectangular cross section. The connector 120 may lock and unlatch or unlock in the same manner as discussed above for the connector 70 of FIGS. 6-10.

Figure 11C:
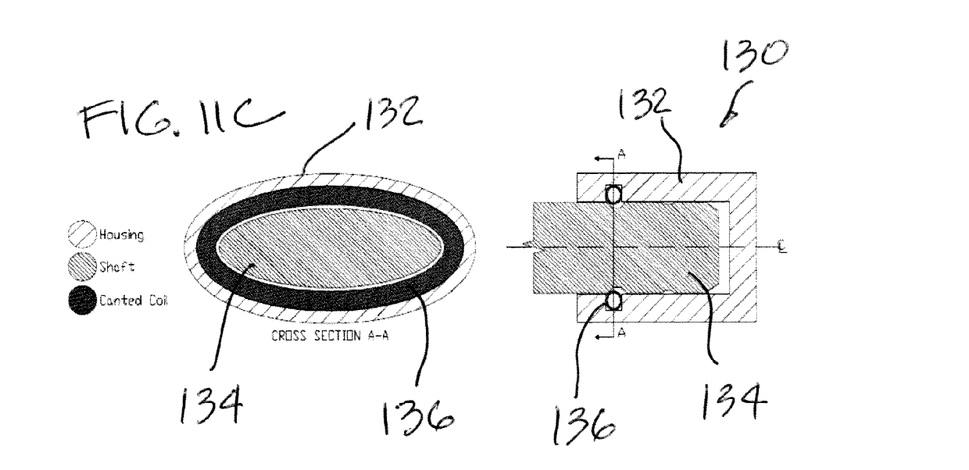
FIG. 11C is a schematic cross-sectional side view and end view of yet another alternative connector.

FIG. 11C shows a side and cross sectional view of a connector 130 having a pin 134, a housing 132, and a spring 136. The pin and the housing have a generally elliptical cross section. The connector 130 may lock and unlatch or unlock in the some manner as discussed above for the connector 70 of FIGS. 6-10.

Figure 11D:
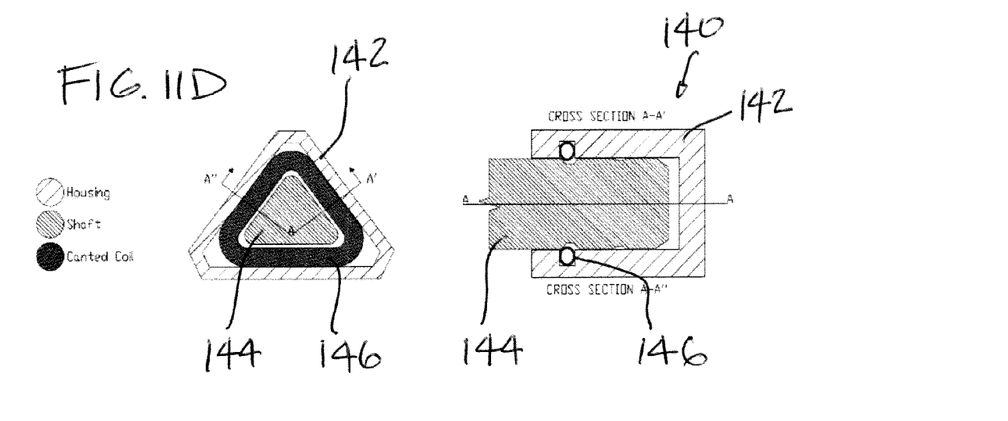
FIG. 11D is a schematic cross-sectional side view and end view of yet another alternative connector.

FIG. 11D shows a side and cross sectional view of a connector 140 having a pin 144, a housing 142, and a spring 146. The pin and the housing have a generally triangular cross section. The connector 140 may lock and unlatch or unlock in the same manner as discussed above for the connector 70 of FIGS. 6-10.

Figure 11E:
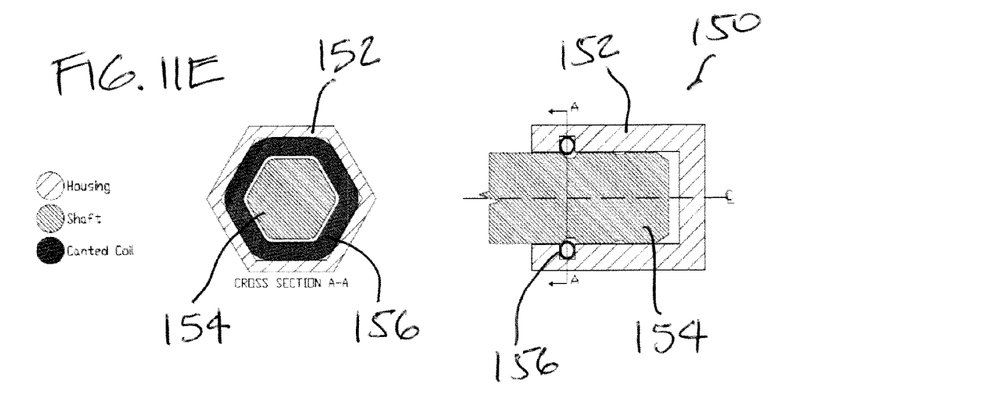
FIG. 11E is a schematic cross-sectional side view and end view of yet another alternative connector.

FIG. 11E shows a side and cross sectional view of a connector 150 having a pin 154, a housing 152, and a spring 156.

The pin and the housing have a generally hexagonal cross section. The connector 150 may lock and unlatch or unlock in the same manner as discussed above for the connector 70 of FIGS. 6-10.

Figure 12:
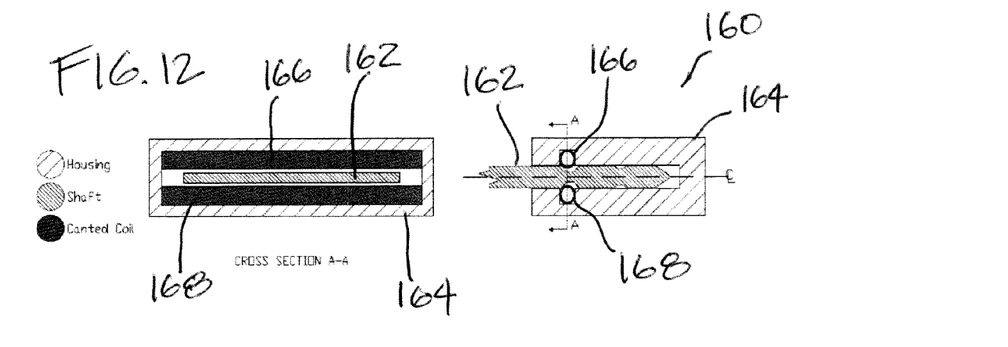
FIG. 12 is a schematic cross-sectional side view and end view of yet another alternative connector.

FIG. 12 shows a side and cross sectional view of a connector 160 having a flange or plate 162, analogous to a cylindrical part, and a housing 164 with both components having a generally rectangular cross section, which is similar to the connector 120 of FIG. 11B with a few exceptions. The present connector 160 has a much wider profile relative to its height. Also, whereas the spring in FIG. 11B is connected or continuous, the present spring are made of at least two separate spring components 166, 168 that are spaced apart from one another. As the springs are separate components, the primary and secondary grooves may optionally incorporate separate sections although continuous grooves are acceptable. The connector 160 may lock and unlatch or unlock in the same manner as discussed above for the connector 70 of FIGS. 6-10. When the part to be inserted into a housing for latching/locking is not a cylindrical part, it is still equivalent to the function of the cylindrical part described herein. The cylindrical part and objects equivalent thereto may generically be referred to as an inserted part.

The various connectors disclosed herein may be used in a number of mechanical applications for locking and unlocking/unlatching where locking and then removal between a first connector component and a second connector component is contemplated. As examples, the connectors may be used to hang objects, to connect objects together, and to secure objects together. As specific examples, the connectors disclosed herein may be used as substitute for screws, such as for assembling cabinets, desks, chairs, etc. Alternatively, the connectors may be used for electrical applications with locking and then unlocking/unlatching. As examples, a first electrical source, such as a car starter, may be connected to the housing and a second electrical source, such as a car battery, may be connected to the cylindrical part and wherein electrical communication between the first electrical source and the second electrical source passes through the housing, the cylindrical part and the spring.

For use in electrical applications, the housing and the inserted part, or first and second connector components, should be made of or at least have sub-parts that are made from a conductive material, such as a copper or copper alloy, brass, or high tensile strength steel, such as stainless steel, with optional plating with a highly conductive material. Likewise, the canted coil spring should be made from a conductive material.

Thus, features of the present device, system, and method include a locking and/or latching mechanism between two bodies, particularly insertion of an inserted part into a housing, which uses a canted coil spring to achieve such locking and/or latching, that consists of at least two grooves (primary and secondary, following one another) in one of the bodies to accept a canted coil spring. In an example, the secondary groove is deeper than the primary groove. In another example, the secondary groove is both deeper and wider than the primary groove.

The locking and/or latching mechanism preferably provides a lock in a reverse direction to prevent removal of the housing and the cylindrical part from one another upon engagement of the canted coil spring into the primary groove. However, upon moving the spring away from the primary groove and later returning to the primary groove, the connector permits unlatching in the reverse direction.

The locking and/or latching mechanism is understood to include a secondary groove that allows the spring to relax and untwist within the housing groove. In an example, the secondary groove does not hold or contain the spring and allow the spring to relax and rotate its major axis.

The locking and/or latching mechanism is understood to include a secondary groove having a shape that allows for a lower removal force as compared to the unlock force to remove the spring when in the primary groove.

The locking and/or latching mechanism may incorporate an inserted part having a cross section of the pin or the housing being rectangular, elliptical, triangular, hexagonal, or polygonal.

The locking and/or latching mechanism may include a spring that is separated into two separate pieces to have two spring sections each with two ends located on different housing sections or inserted part sections.

The above description presents the best mode contemplated for carrying out the present connectors, systems, and associated methods, and of the manner and process of making and using them, in such full, clear, concise, and exact terms as to enable any person skilled in the art to which it pertains to make and use these connectors, systems, and associated methods. These connectors, systems, and associated methods are, however, susceptible to modifications and alternate constructions from that discussed above that are fully equivalent. Consequently, these connectors, systems, and associated methods are not limited to the particular embodiments disclosed. On the contrary, these connectors, systems, and associated methods cover all modifications and alternate constructions coming within the spirit and scope of the connectors, systems, and associated methods as generally expressed by the following claims, which particularly point out and distinctly claim the subject matter of the connectors, systems, and associated methods.

What is claimed is:

1. A connector comprising a first connector component for mating with a second connector component, a groove located in or on the first connector component or the second connector component and a pair of grooves located in or on the other one of the first connector component or the second connector component;
    the groove having two sidewalls and a flat bottom wall;
    the pair of grooves comprises a first groove having a first depth and a second groove having a second depth, which differs from the first depth; and
    wherein a canted coil spring is positioned in the first groove and the groove and is movable to be seated in the second groove and the groove.

2. The connector of claim 1, wherein the first connector component is in electrical communication with a first source and the second connector component is in electrical communication with a second source.

3. The connector of claim 2, wherein the canted coil spring is made from a copper material, a copper alloy material, a high tensile strength steel, or combination thereof.

4. The connector of claim 2, wherein the canted coil spring is coated with a conductive material.

5. The connector of claim 1, wherein the first connector component is a pin and the second component is a housing, which has a bore for receiving the pin.

6. The connector of claim 1, wherein the first component is a housing and the second component is a pin, and wherein the housing comprises a bore for receiving the pin.

7. The connector of claim 1, wherein the second groove comprises at least one tapered side wall.

8. The connector of claim 1, wherein the second groove is both wider and deeper than the first groove.

9. A method for using a connector comprising
moving a first connector component relative to a second connector component to position a canted coil spring in a first groove for locking;
moving the canted coil spring to a location adjacent the first groove for holding,
moving the canted coil spring to a second groove for latching,
moving the canted coil spring back to the first groove; and
wherein the first connector component or the second connector component comprises a groove having two side walls and a flat bottom groove.

10. The method of claim 9, further comprising separating the first connector component from the second connector component.

11. The method of claim 9, wherein the second component comprises both the first groove and the second groove.

12. The method of claim 11, wherein the second groove has a larger depth than the first groove.

13. The method of claim 9, wherein the first component comprises both the first groove and the second groove.

14. The method of claim 9, wherein the first component, the second component, and the spring all comprise an electrically conductive material.

15. A connector comprising:
a housing comprising a bore and a housing groove having a housing groove configuration;
a pin comprising a pin groove having a pin groove configuration;
an axial canted coil spring disposed in the bore in a first spring position defined by a combination of the housing groove and the pin groove;
a second groove located adjacent the housing groove or the pin groove, the second groove having a second groove configuration with a second groove depth that differs from the housing groove configuration and the pin groove configuration; and
wherein the canted coil spring is movable relative to the pin and the housing.

16. The connector of claim 15, wherein the second groove is located on the pin and adjacent the pin groove.

17. The connector of claim 15, wherein the second groove is located in the bore of the housing, adjacent the housing groove.

18. The connector of claim 15, wherein the canted coil spring is rotatable relative to the housing by rotating from a first turn angle when in the first spring position to a second turn angle when in a second spring position.

19. The connector of claim 15, wherein the pin is movable in a first direction but not a second, opposite, direction when the canted coil spring is in the first spring position.

20. The connector of claim 19, wherein the pin is movable in the second direction when the canted coil spring is in a second spring position, which is defined at least in part by the second groove.

21. The connector of claim 15, wherein the housing groove configuration comprises a bottom wall and two sidewalls.

22. The connector of claim 21, wherein the two sidewalls are generally parallel to one another.

23. The connector of claim 22, wherein the bottom wall is angled relative to the two sidewalls.

24. The connector of claim 15, wherein the pin has a round cross-section, a square cross-section, a rectangular cross-section, an oval cross-section, a polygonal cross-section, or a triangular cross-section.

\* \* \* \* \*

UNITED STATES PATENT AND TRADEMARK OFFICE
CERTIFICATE OF CORRECTION

PATENT NO.         : 8,366,475 B2                              Page 1 of 1
APPLICATION NO.    : 13/239153
DATED              : February 5, 2013
INVENTOR(S)        : Smith et al.

It is certified that error appears in the above-identified patent and that said Letters Patent is hereby corrected as shown below:

In the Specification

Column 3, line 67, delete "FIG.S," and insert -- FIGs., --, therefor.

Column 10, line 40, delete "some" and insert -- same --, therefor.

Column 10, line 58, delete "some" and insert -- same --, therefor.

Signed and Sealed this
Twenty-first Day of October, 2014

Michelle K. Lee
*Deputy Director of the United States Patent and Trademark Office*